Figure 1:
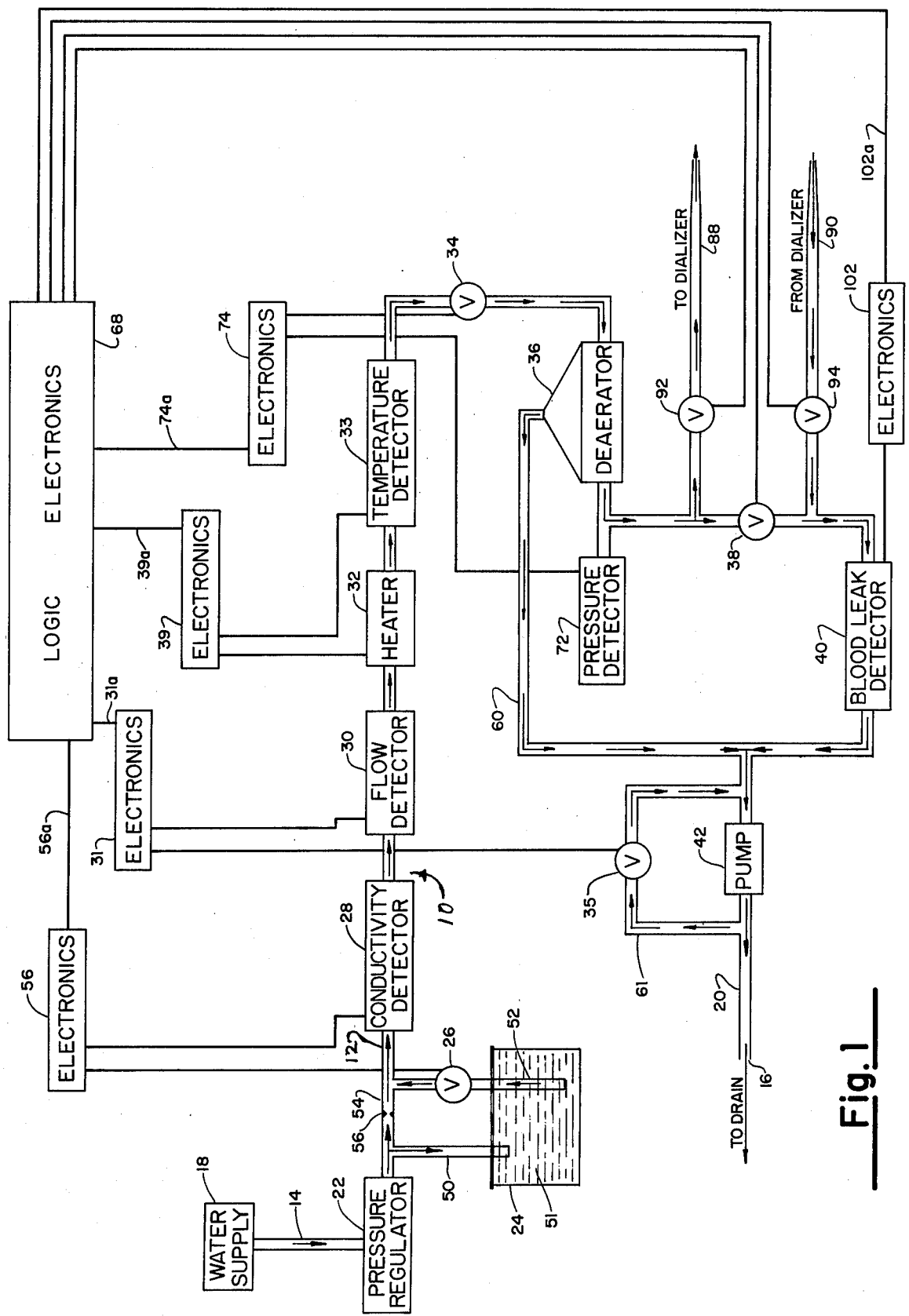

United States Patent [19]

Eaton

[11] 4,060,485
[45] Nov. 29, 1977

[54] DIALYSIS APPARATUS

[75] Inventor: Thomas Eaton, Hawthorne, Calif.

[73] Assignee: I T L Technology, Inc., Hawthorne, Calif.

[21] Appl. No.: 585,074

[22] Filed: June 9, 1975

[51] Int. Cl.² .................. B01D 31/00; B01D 13/00
[52] U.S. Cl. .................................. 210/87; 210/90; 210/96 M; 210/321 B
[58] Field of Search ............... 210/22, 321 K, 87, 96, 210/90; 137/93

[56] References Cited

U.S. PATENT DOCUMENTS

| | | | |
|---|---|---|---|
| 3,073,330 | 1/1963 | Fattor | 137/93 |
| 3,441,136 | 4/1969 | Serfass et al. | 210/96 M X |
| 3,508,656 | 4/1970 | Serfass et al. | 210/90 |
| 3,690,340 | 9/1972 | Sipin | 137/93 |
| 3,878,095 | 4/1975 | Frasier | 210/96 M X |

*Primary Examiner*—Frank A. Spear, Jr.
*Attorney, Agent, or Firm*—Edward H. Loveman

[57] ABSTRACT

A dialysis apparatus, comprising an elongated flow passage with a water inlet and a brine outlet end, a pump at the outlet end for draining brine from the passage, a reservoir of brine concentrate in the passage, means for diluting the brine with water and adjusting salinity of the brine solution in the passage, a heater in the passage downstream of the reservoir for heating the brine solution after its salinity has been stabilized, a deaerator in the passage for breaking up the brine bubbles and removing air therefrom, a blood dialysis unit connected to the passage for purifying the blood of a patient whose bloodstream is connected to the unit, and pressure adjustment means connected to the passage for adjusting the pressure of brine passing to the unit.

9 Claims, 1 Drawing Figure

1

DIALYSIS APPARATUS

This invention concerns an improved system and apparatus for treating the blood of a person suffering from inadequate kidney function, and is of the type of apparatus generally known as a dialysis system, or more popularly, an artificial kidney machine.

The invention more particularly concerns improvements over those described in my prior U.S. Pat. No. 3,814,249 entitled "Dialysis Apparatus," issued June 4, 1974. The prior apparatus described in said patent is highly successful in that it is a small, selfcontained, portable economical, to manufacture, and operable by a person requiring dialytic treatment, or by an attendant with no special skill or training. The prior apparatus has one characteristic which limits its use to some extent, in that it requires a Kiil type of artificial kidney device.

The Kiil device is well known. It consists of a pair of sheet-like membranes with opposing inner surfaces between which the blood being treated is circulated. The sheets are arranged between a pair of plate-like members having opposing brine conducting channels. The brine is circulated through the channels under a controlled pressure less than the pressure of the blood being treated, with the result that the membranes are drawn a predetermined extent into the channels in the plates to define blood conducting channels in and between the sheets. The negative or minus pressure imposed upon the brine serves to control the rate at which dialysis takes place.

Lately there has come into general use an improved coil type dialysis device in tubular form. Such devices are manufactured and distributed by a number of manufacturers. Typical coil type dialysis devices are described in U.S. Pat. No. 3,508,662 issued Apr. 28, 1970 and U.S. Pat. No. 3,741,395 issued June 26, 1973. The coil type of dialysis device employs a helically wrapped membrane and supporting mesh and has a number of advantages over the Kiil type of dialysis device. Unfortunately, it cannot be used in the dialysis apparatus described in U.S. Pat. No. 3,814,249 abovementioned because the coil type of dialysis device must operate at a positive pressure above atmosphere and above that of the blood being treated, while the system disclosed in U.S. Pat. No. 3,814,249 necessarily operates at negative or subatmospheric pressure as described in the patent.

The present invention is directed at a number of improvements in the prior dialysis apparatus of U.S. Pat. No. 3,814,249 such as positioning the heating unit downstream of the brine and the water mixing station to obtain a more positive control of the salinity of the solution and still make it possible to utilize many of the other advantages of the apparatus, and at the same time to employ a coil type dialysis device.

It is therefore a principal object of the present invention to provide a dialysis system which can be operated with either a coil or Kiil dialysis device.

These and other objects and many of the attendant advantages of this invention will be readily appreciated as the same becomes better understood by reference to the following detailed description when considered in connection with the accompanying drawings in which:

FIG. 1 illustrates diagrammatically my improved dialysis apparatus employing the present invention.

Referring now to the drawings wherein like reference characters designate like or corresponding parts throughout, there is illustrated in FIG. 1 a dialysis apparatus generally designated as reference numeral 10 including an elongated fluid conducting flow line or passage 12, having an inlet end 14 and a discharge end 16.

The inlet 14 of the passage 12 is adapted to connect with a suitable water supply 18 of warm or cold water. The water supply 18 may be pressurized municipal water service, storage tank or vessel, or any other suitable and available source of water. The discharge end 16 of the passage 12 discharges waste or spent fluid through a discharge hose 20 which can be connected with a suitable external drain or waste pipe (not shown).

Arranged in the flow passage 12, between the ends thereof and progressing from the inlet to the discharge ends thereof, is a pressure regulator 22, a sealed reservoir 24, a variable flow valve 26, a salinity or conductivity detector 28, a flow rate detector 30, a heater 32, a temperature detector 33, a pressure valve 34, a deaerator 36, a control valve 38, a blood leak detector 40 and a pump 42.

The pressure regulator 22 is adapted to limit and regulate the pressure of the water introduced into the inlet end of the system 10. The pressure regulator 22 can be of conventional type and feeds water into the reservoir 24 near the top thereof via an input tube 50. The sealed reservoir 24 contains a brine concentrate 51 which is forced to flow by the water pressure from the reservoir 24 through an output tube 52 which is open near the bottom of the reservoir 24. The valve 26 is located in the tube 52 and is electrically operable by the salinity or conductivity detector 28. The valve 26 may be a conventional electromechanical valve such as described in my copending U.S. Pat. application No. 569,597 filed 4/21/75 now U.S. Pat. No. 3,991,972 issued Nov. 16, 1976. A bypass pipe 54 which has a restrictor or orifice 56 connects the tube 50 and 52 for passing fresh water directly into the brine stream flowing to the conductivity detector 28. Thus, the water supply 18 delivers water through the pressure regulator 22 to the orifice 56 and also to the reservoir 24. Since the pressure on the reservoir 24 is greater than the pressure of the brine solution at the output of the conductivity valve 26 (due to the restriction or orifice 56) the brine flows through the valve 26 where it is mixed with the water flowing through the orifice 56 and the mixture or brine solution (brine and water) enters the conductivity detector 28.

The conductivity detector 28 operates by measuring the conductivity of the brine solution passing through it and passes this information via an electrical signal to an electronics 56 which compares it with a reference. If the result is either high or low, the electronics 56 sends a signal to the conductivity valve 26 to close or open it respectively, thereby adjusting the conductivity of the brine solution (dialysate) to that of the reference. Although not illustrated, the electronics 56 may include lamps and/or audio means for indicating when the conductivity of the brine solution is higher or lower than the reference. The electronics 56 also has an output 56a which is connected to a logic electronics 68, the purpose of which will hereinafter be more fully described. The conductivity detector 28 may be of conventional type or such as described in my copending U.S. Pat. application No. 569,940 filed 4-21-75, now abandoned.

The flow rate detector 30 measures the rate of liquid flowing to the heater 32 and sends a signal indicative of the flow to the electronics 31 which compares the signal with a reference or desired flow. If the resultant is either high or low, the electronics 31 sends a signal to the bypass valve 35 to open or close respectively and thereby control the flow of liquid in the passage 12 by controlling the flow in a bypass pipe 61. The flow detector 30 may be of a conventional type such as described in my copending patent application Ser. No. 570,029 filed Apr. 21, 1975, and entitled "Fluid Flow Rate Detector."

The heater 32 is located downstream of the flow rate detector 30 and heats the brine solution in accordance with the difference between a reference or desired temperature in a electronics 39 and the temperature sensed by the temperature detector 33. It should be noted that the heater 32 heats the brine solution after its salinity or condutivity has been stabilized by the conductivity detector 28, the electronics 56 and the valve 26. This is an important feature of the invention inasmuch as in the prior system described in U.S. Pat. No. 3,814,249 the incoming water was heated prior to mixing with the brine concentrate. When heated the water and brine concentrate were mixed together and the temperature of the solution was different from either the water or the brine concentrate before mixing, such that the conductivity of the solution was undeterminate and unstable. In the present system, the conductivity of the solution is stabilized and then it is heated.

A bypass pipe 60 is connected between the top of the deaerator and the inlet to the pump 42 to remove air from the solution. Within the dearator 36 is a baffle having a relatively small aperture (not shown) to liberate air with a relatively high velocity and when all the air is gone to permit relatively little fluid flow through the bypass pipe 60. The high velocity air flow through the bypass pipe 60 is obtained by connecting the discharge of the pipe 60 to the inlet of the pump 42 where there is a maximum negative pressure. A pressure detector 72 is located on the downstream side of the deaerator and sends its information to an electronics 74 which compares it with a reference therein to control the valve 34 in a fashion similar to the electronics 56, 31 and 39 hereinbefore discussed.

A dialyzer unit or device (not shown) is coupled to the passage 12 between the deaerator 36 and the blood detector 40. This dialysis device may be of the coil type and have a reservoiror tank open to atmospheric pressure. The brine solution may be connected to feed into the reservoir via a tube 88. Immersed in the brine in the reservoir may be a coiled dialysis element of the type disclosed in Miller U.S. Pat. No. 3,508,662, which is adapted to be connected to a patient undergoing treatment. An output tube 90 may connect the top of the reservoir or tank with the passage 12. The dialysate unit may alternatively be the conventional Kiil type as described in the abovementioned U.S. Pat. No. 3,814,249. The present system is versatile so that it may be operated at positive or negative pressure, depending on the type of dialysis unit employed, as contrasted with the prior system of U.S. Pat. No. 3,814,249 which is limited to use of a Kiil unit operating under negative pressure.

The logic electronics 68 is utilized to energized the electric valves 92, 94 and 38, which control the flow of fluid to a dialyzer (not shown). Under standby conditions, the valves 92 and 94 are closed and the valve 38 is open, to permit the flow rate therethrough. When a dialysis treatment is to be performed, a manual signal (not shown) is applied to the logic electronics 68 which sends signals to close the valve 38 and open the valves 92 and 94. The flow rate of fluid is now to the dialyzer via line 88 and returns from the dialyzer via line 90. If at any time during the dialysis treatment, any of the electronics 56, 31, 39, or 74 determine a condition, which is either high or low relating to the respective function, the respective electronic will activate the logic electronic 68 via respective lines 56a, 31a, 39a or 74a, to send out signals to open the valve 38 and close the valves 92 and 94. Similarly, if the blood leak detector 40 indicates a blood leak condition, a signal is sent to the electronics 102. If the signal from the detector 40 persists for a fixed time period i.e. 10 seconds, the electronics 102 sends a signal via line 102a to the logic electronic 68 which will send out signals to open the valve 38 and close the valves 92 and 94.

The blood leak detector 40 is of a conventional type such as described in the abovementioned U.S. Pat. No. 3,814,249. It contains photoelectric means for detecting the presence of blood in the brine solution which indicates leakage or malfunction of the dialysis unit. Upon detecting such blood leakage, the blood detector 40 sends the information to the electronics 102 which provides an output to the logic electronics 68 via the line 102a, as mentioned above. A signal lamp and/or audible means may be connected to the blood leak detector 40 to indicate that blood leakage has occurred when the information is sent to the logic electronics 68. It should be understood that although not shown the electronics 56, 31, 39, 74 and 68 may each have individual power supplies or they may all get power from one electronics or from another single source, etc.

In operation of the apparatus 10, the tubes 88 and 90 will be connected to a dialyzer. The water supply 18 is connected to the pressure regulator 14 which adjusts the pressure to permit the brine to flow and to the value required for operating the dialysis unit. The conductivity detector 28 operates by measuring the conductivity of the brine solution passing therethrough and controls the valve 26 via electronics 56 to adjust the brine flow passing to the passage 12. The restricted tube 54 provides fresh water to dilute the brine concentrate. Following the conductivity detector 28, the brine solution is heated by the heater 32. The flow detector 30, preceding the heater 32, operates to control the flow of brine solution in the passage 12 by controlling the flow in the bypass pipe 61.

The heater 32 provides a brine solution of proper temperature to a dialysis unit (not shown) for efficient operation thereof in cleaning the blood in passing therethrough. The pressure detector 72 and the valve 34 together with the electronics 74, insure that the brine solution is supplied to the dialysis unit at the correct pressure. This may be less than the pressure of the blood stream, if a Kiil device is used at negative pressure, or if a coil type is used, the brine pressure will be positive or higher than atmospheric pressure.

The brine and other products separated from the patients blood stream pass out of the dialyzer via pipe 90 and pass through the blood leak detector 40 and the pump 42 to the drain 20.

To summarize, each of the electronics 56, 31, 39, 74 and 102, may have audible and/or lamp devices for indicating the respective function problem which will trigger the logic electronics to disconnect the dialyzer from the passage 12 by opening the valve 38 and closing the valves 92 and 94.

It should be understood that the foregoing relates to only a preferred embodiment of the invention, and that it is intended to cover all changes and modifications of the example of the invention herein chosen for the purposes of the disclosure, which do not constitute departures from the spirit and scope of the invention.

The invention claimed is:

1. A dialysis apparatus comprising:
an elongated flow passage having a water inlet at one end and a fluid discharge at the other end;
a reservoir containing a brine concentrate said reservoir communicating with portions of said passage downstream of said water inlet so that water enters said reservoir to force said brine concentrate out of said reservoir and into said passage;
a water inlet tube connected between said passage and said reservoir and in direct communication with said brine concentrate in said reservoir;
a brine outlet tube connected to said reservoir and to said passage downstream of said water inlet tube;
a restrictor means in said passage between said water inlet tube and said brine outlet tube for permitting water to flow therethrough at a pressure lower than the water pressure applied to said water inlet tube whereby said brine concentrate entering said passage from said brine outlet tube will be diluted by the water passing through said restrictor means to form a brine solution;
a conductivity detector means in said passage downstream of said brine outlet tube for detecting changes in the conductivity of said brine solution;
valve means in said brine outlet tube operable by said conductivity detector means for controlling flow of said brine concentrate through said brine outlet tube;
spaced inlet and outlet tubes connected to said passage downstream from said conductivity detector means for connecting a blood dialyzer device to said passage; and
a pump downstream of said dialyzer device having an inlet connected to said passage for drawing said brine solution through said dialyzer and an outlet for discharging said brine solution to a drain.

2. A dialysis apparatus as defind in claim 1, further comprising:
a temperature detector means in said passage downstream of said brine outlet tube for detecting the temperature of said brine solution; and
heater means located in said passage between said brine outlet tube and said temperature detector means and operable by said temperature detector means for controlling the temperature of said brine solution in said passage to a preselected value.

3. A dialysis apparatus as defined in claim 2, further comprising:
a bypass pipe connected between said inlet and said outlet of said pump;
a flow detector means in said passage between said heater and said brine outlet tube for detecting said flow of brine solution therein; and
valve means in said bypass pipe operable by said flow detector means controlling the flow of said brine solution in said passage to a preselected value.

4. A dialysis apparatus as defined in claim 2, further comprising:

a deaerator connected in said passage downstream of said temperature detector and arranged to collapse air bubbles therein; and
a conduit means for conducting the air from the collapsed air bubbles to said pump inlet.

5. A dialysis apparatus as defined in claim 4, further comprising:
conductivity detector means in said passage between said brine outlet tube and said heater means for detecting changes in the conductivity of said brine solution from a preselected value; and
a valve means in said brine outlet tube, operable by said conductivity detector means for controlling flow of said brine concentrate through said brine outlet tube.

6. A dialysis apparatus as defind in claim 5, further comprising:
a deaerator connected in said passage downstream of said temperature detector and arranged to collapse air bubbles therein; and
a conduit means for connecting the air from the collapsed air bubbles to said pump inlet.

7. A dialysis apparatus as defined in claim 6, further comprising:
a pressure detector connected to said passage downstream of said deaerator for sensing the pressure of said brine solution in said passage; and
a valve means in said passage between said temperature detector and said deaerator and operable by said pressure detector for adjusting the pressure of said brine solution in said passage to a value required by said blood dialyzer unit.

8. A dialysis apparatus as defined in claim 7, further comprising:
a shutoff valve means in said passage between said spaced inlet and outlet tubes;
a second shutoff valve means located in said spaced inlet tube;
a third shutoff valve means located in said spaced outlet tube; and
a logic electronic means coupled to said conductivity detector means, said temperature detector means, said flow detector means and said pressure detector means and operable when any of said detector means indicate values in excess of said preselected value respectively to close said shutoff valve means and open said second shutoff valve means and said third shutoff valve means thereby preventing said brine solution from flowing through said blood dialyzer unit.

9. A dialysis apparatus as defined in claim 2, further comprising:
a pressure detector connected to said passage downstream of said temperature detector for sensing the pressure of said brine solution in said passage; and
a valve means in said passage between said pressure detector and said temperature detector and operable by said pressure detector to adjust the pressure of said brine solution in said passage to a preselected value required by said blood dialyzer unit.

* * * * *